(12) United States Patent
Chiang

(10) Patent No.: US 10,898,688 B2
(45) Date of Patent: Jan. 26, 2021

(54) NEEDLELESS CONNECTOR LOOSENING DEVICE

(71) Applicant: Te Chih Chiang, Langley (CA)

(72) Inventor: Te Chih Chiang, Langley (CA)

(*) Notice: Subject to any disclaimer, the term of this patent is extended or adjusted under 35 U.S.C. 154(b) by 0 days.

(21) Appl. No.: 16/781,430

(22) Filed: Feb. 4, 2020

(65) Prior Publication Data

US 2020/0246593 A1    Aug. 6, 2020

Related U.S. Application Data

(60) Provisional application No. 62/801,564, filed on Feb. 5, 2019.

(51) Int. Cl.
*A61M 25/02* (2006.01)
*A61M 39/10* (2006.01)

(52) U.S. Cl.
CPC ........ *A61M 25/02* (2013.01); *A61M 39/1011* (2013.01); *A61M 2025/028* (2013.01)

(58) Field of Classification Search
CPC .......... A61M 25/0014; A61M 39/1055; A61M 39/10; A61M 39/1011; B25B 13/065; B25B 13/48
See application file for complete search history.

(56) References Cited

U.S. PATENT DOCUMENTS

| | | | |
|---|---|---|---|
| 5,297,458 A | 3/1994 | Smith | |
| 6,817,272 B2 * | 11/2004 | Holland | H01R 43/26 439/304 |
| 7,024,968 B2 * | 4/2006 | Raudabough | A61M 5/347 81/121.1 |
| 2006/0130617 A1 | 6/2006 | Mamourian | |
| 2018/0071897 A1 | 3/2018 | Banko | |

FOREIGN PATENT DOCUMENTS

| | | |
|---|---|---|
| CN | 203371437 U | 1/2014 |
| KR | 2014-0042069 A | 4/2014 |
| WO | 2018/138327 A1 | 8/2018 |

* cited by examiner

*Primary Examiner* — Deanna K Hall
(74) *Attorney, Agent, or Firm* — Oyen Wiggs Green & Mutala LLP

(57) ABSTRACT

A tool for loosening a needleless connector is provided. The tool is a holder for holding a catheter port connected to the needleless connector. The holder includes a front surface, a rear surface, a top surface, and a cavity. The cavity accommodates the catheter port. The cavity extends through the holder and has a front opening in the front surface, a rear opening in the rear surface, and a rear inner wall. The cavity is defined by at least a first cross-sectional dimension and a second cross-sectional dimension, the first cross-sectional dimension at least partially defining a front section opening to the front opening, the second cross-sectional dimension at least partially defining a rear section opening to the rear opening.

13 Claims, 11 Drawing Sheets

NEEDLELESS CONNECTOR LOOSENING DEVICE

TECHNICAL FIELD

The present invention relates to a tool for loosening a needleless connector connected to the end of a central venous catheter.

BACKGROUND

Central venous catheters (CVCs) are one of the most commonly used devices to deliver intravenous therapies such as chemotherapy, antibiotics, and parenteral nutrition when long term secure venous access is required. Examples of CVCs include the peripherally inserted central catheter (PICC) and tunnelled central venous catheter (tunnelled CVC). Use of PICC, for example, due to its ease of insertion, safety and cost-effectiveness, has become ubiquitous in health care, including oncology.

Line migration is one of the more common and costly complications of CVCs, including PICC. PICC line migration for example, is reported at a rate of 1-5%, but may occur at a higher rate in different hospitals. Regarding PICC line migration, two studies have documented as much as a 9 mm of movement of the distal end with respiration and 21 mm of movement of the distal end with abduction and adduction of the arm; coughing and vomiting have been also identified as potential risk factors for migration. Securing devices have been used to prevent line migration and were associated with cost-saving related to prevention of re-insertion.

One of the iatrogenic causes of line migration is movement during the attempt to disconnect with a twisting motion the needleless connector threadably connected to the catheter port at the proximal end of the catheter line. To disconnect the needleless connector, the healthcare worker or patient uses one hand to grasp the catheter port (e.g. a catheter port, a hub, etc.) to hold the catheter steady, and twists the needleless connector with the other hand. Often, an adhesion between the catheter port and the needleless connector due to fluid, drug, blood or fibrin makes the twisting motion extremely difficult. Forcibly twisting seized needleless connectors often leads to inadvertent pulling on the catheter, resulting in line migration. Damage to the catheter port can also occur, necessitating replacement of the entire catheter. Healthcare workers who regularly disconnecting needleless connectors have reported suffering from muscle injury and carpal tunnel syndrome associated with the twisting.

There is a general desire for apparatus for safely and efficiently loosening and disconnecting needleless connectors from catheter ports of catheters.

The foregoing examples of the related art and limitations related thereto are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

One aspect of the invention provides a tool for loosening a needleless connector is provided. The tool is a holder for holding a catheter port connected to the needleless connector. The holder includes a front surface, a rear surface, a top surface, and a cavity. The cavity accommodates the catheter port. The cavity extends through the holder and has a front opening in the front surface, a rear opening in the rear surface, and a rear inner wall. The cavity is defined by at least a first cross-sectional dimension and a second cross-sectional dimension, the first cross-sectional dimension at least partially defining a front section opening to the front opening, the second cross-sectional dimension at least partially defining a rear section opening to the rear opening. The first cross-sectional dimension is greater in area than the second cross-sectional dimension. The rear inner wall defines the narrowing of the front section to the rear section. The first cross-sectional dimension has an aspect ratio of greater than 1. The front section frictionally or lockingly engages the catheter port. The holder also has a slot in the top surface extending from the front surface to the rear surface, the slot adjoining the cavity.

The first cross-sectional dimension may be constant along the front section, and the second cross-sectional dimension may be constant along the rear section.

The rear inner wall may be parallel to the front surface and the rear surface.

The first cross-sectional dimension may have an aspect ratio of at least 4:3.

The first cross-sectional dimension may have a central portion with opposing wing portions.

The cross-sectional profile of the holder may be an oval or a rectangle having an aspect ratio of at least 3:2.

The front section and the rear section of the cavity may be co-axial.

The slot may be centrally aligned above the cavity.

The width of the slot may be constant from the front surface to the rear surface of the holder.

The width of the slot may be less than a half of a width of the first cross-sectional dimension.

Corners between the front opening and the cavity, between the rear opening and the cavity, between the slot and the top surface, and between the slot and the cavity, may be bevelled or rounded.

Another aspect of the invention provides a tool comprising a holder as described herein and further including a wrench for gripping the needleless connector, the wrench comprising a front surface, a rear surface, and a through hole. The through hole may be configured to frictionally or lockingly engage the needleless connector.

In addition to the exemplary aspects and embodiments described above, further aspects and embodiments will become apparent by reference to the drawings and by study of the following detailed descriptions.

BRIEF DESCRIPTION OF THE DRAWINGS

Exemplary embodiments are illustrated in referenced figures of the drawings. It is intended that the embodiments and figures disclosed herein are to be considered illustrative rather than restrictive.

FIGS. 1A to 10 are images of prior art catheter assemblies with different types of catheter ports. FIG. 1A shows a needleless connector attached to a bulb catheter port on a catheter line. FIG. 1B shows a winged valve on a catheter line. FIG. 1C shows a winged hub on a clamped catheter line.

FIG. 2 is a front perspective view of a holder according to an embodiment of the invention.

FIG. 3 is a front view of a holder according to the embodiment shown in FIG. 1.

FIG. 4 is a sectional front perspective view of a holder according to the embodiment shown in FIG. 1.

FIG. 5 is a rear perspective view of a holder according to the embodiment shown in FIG. 1.

FIG. 6 is a front perspective view of a wrench and holder combination according to an embodiment of the invention.

FIG. 7 is a rear perspective view of a wrench and holder combination according to the embodiment shown in FIG. 6.

FIG. 8 is a top view of a wrench and holder combination according to the embodiment shown in FIG. 6.

FIG. 9 is a front view of a wrench according to the embodiment shown in FIG. 6.

DESCRIPTION

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

The term "catheter" as used herein refers to any catheter that uses a needleless connector, including peripherally inserted central catheters (PICC) and tunneled central venous catheters.

The term "distal" as used herein refers to a direction that is generally towards a target site of the catheter within a patient's anatomy.

The term "catheter port" as used herein refers to the device at the proximal end of a catheter line that threadably connects to the needleless connector. Examples of catheter ports include valves (e.g. bulb valves, winged valves) and valveless hubs (e.g. winged hubs).

The term "proximal" as used herein a direction that is generally away from a target site of the catheter within a patient's anatomy.

Figure 1:
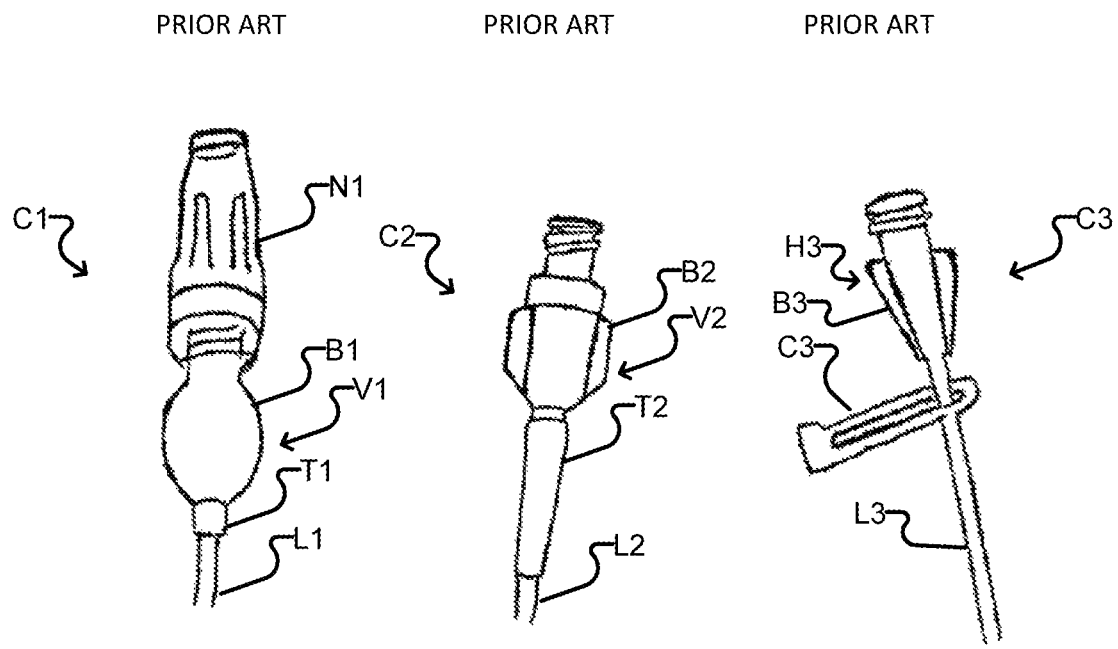
Figure 2:
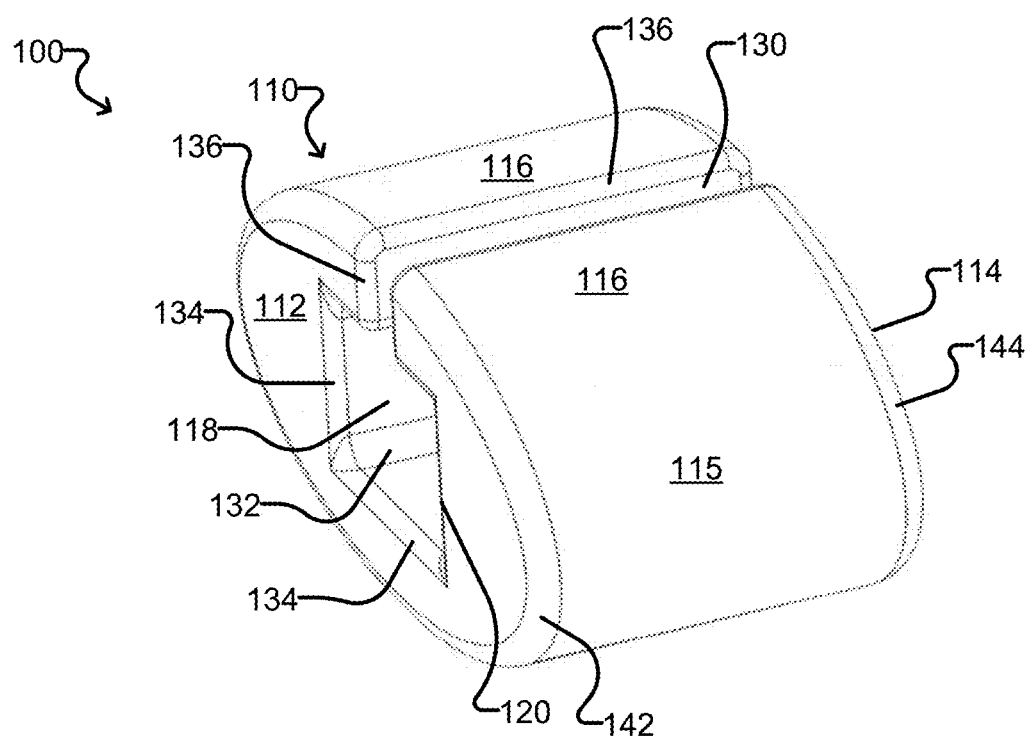
Figure 3:
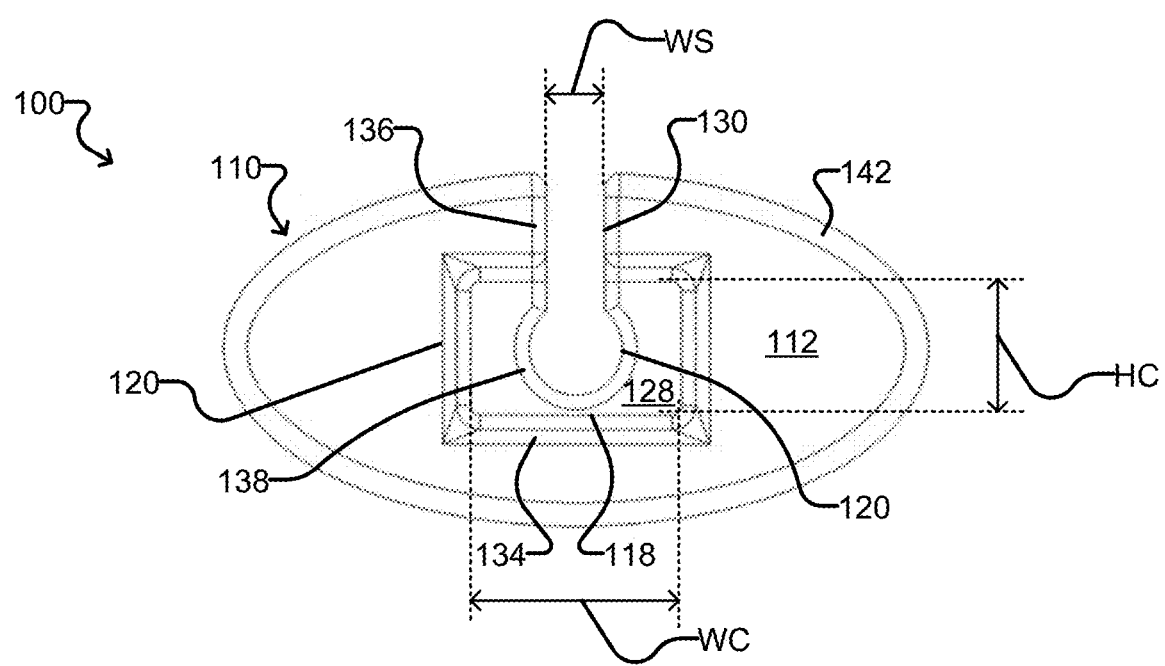
Figure 4:
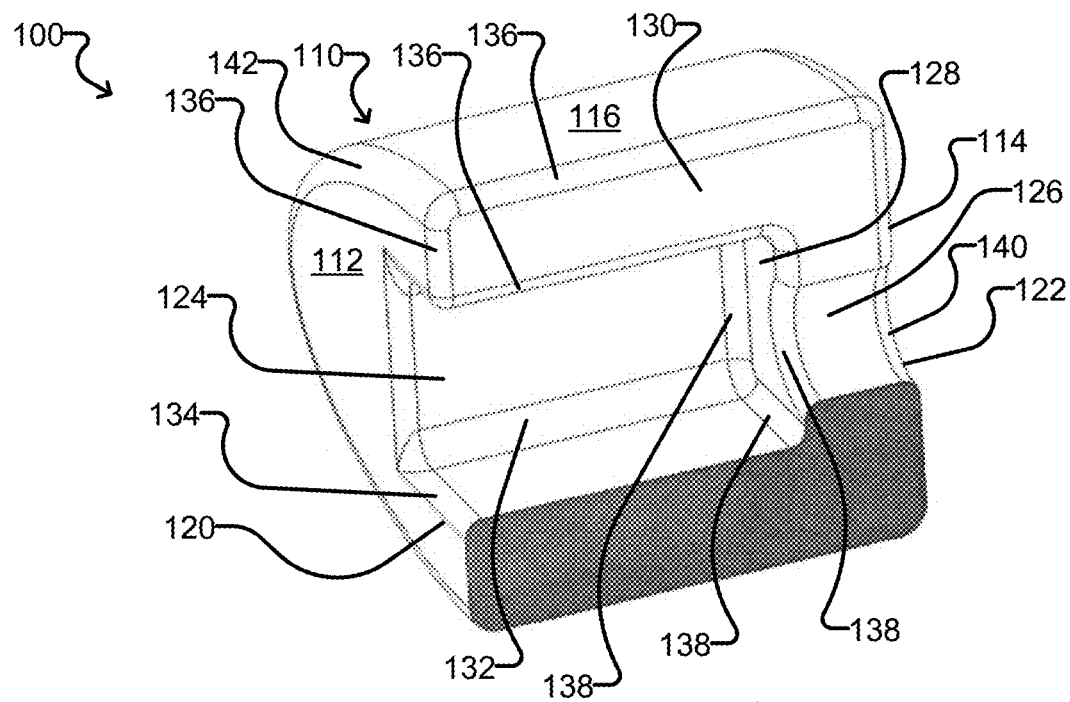
Figure 5:
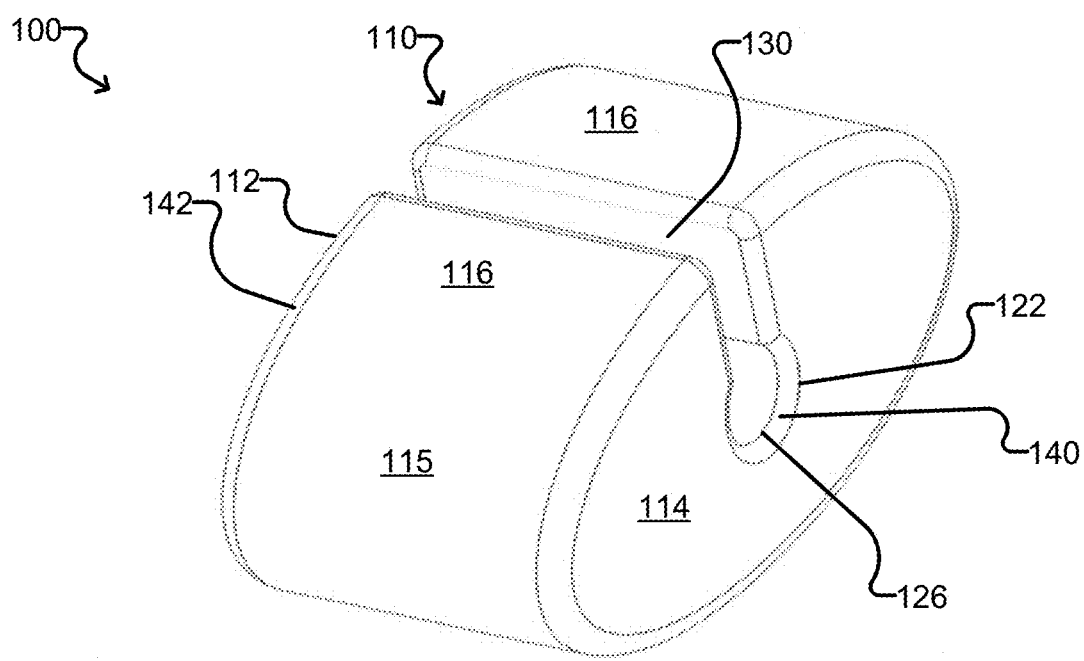
Figure 6:
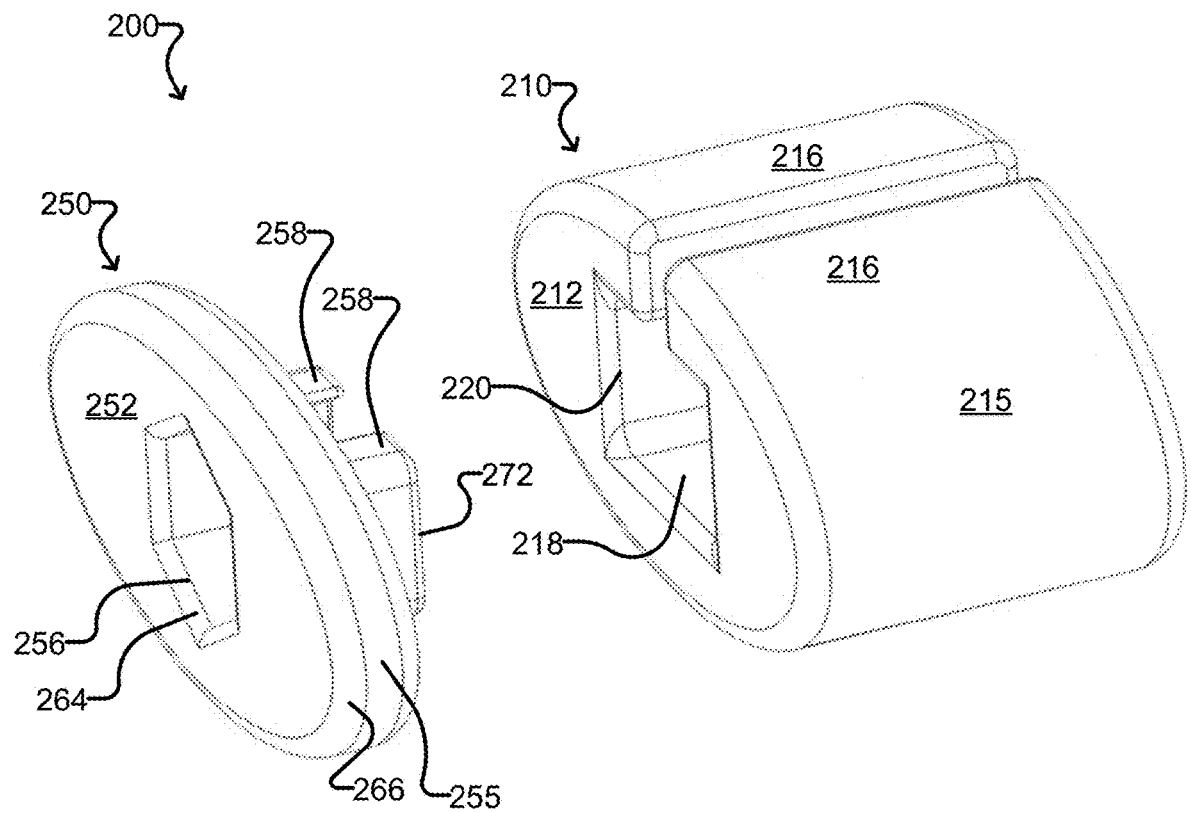
Figure 7:
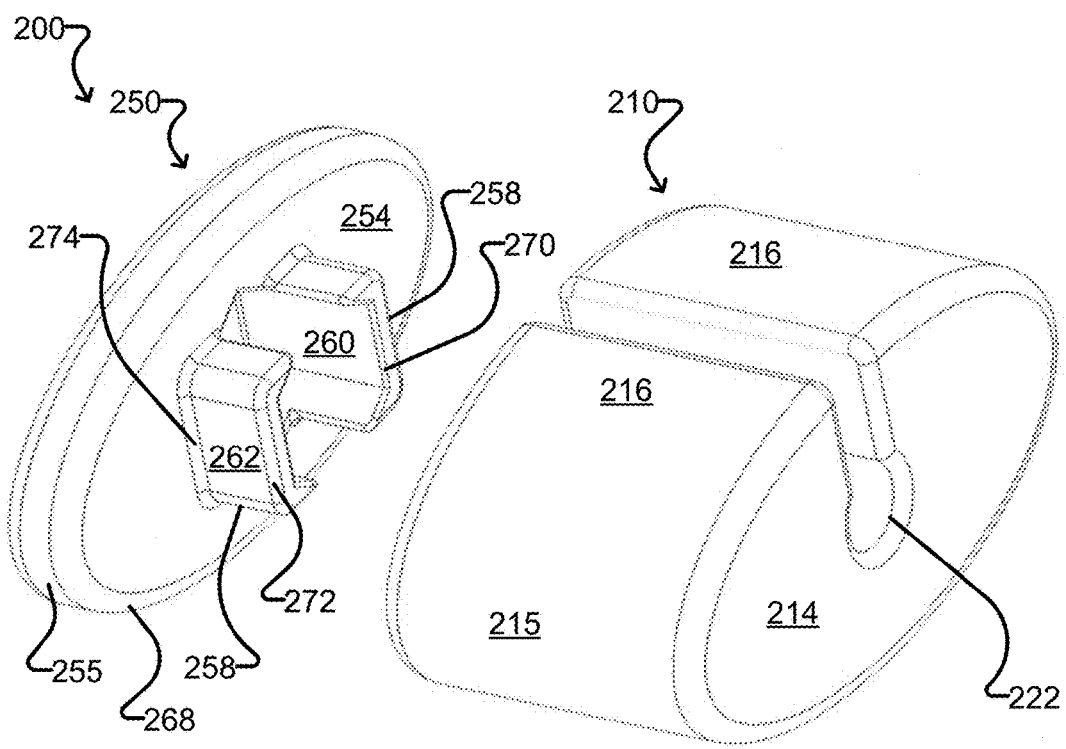
Figure 8:
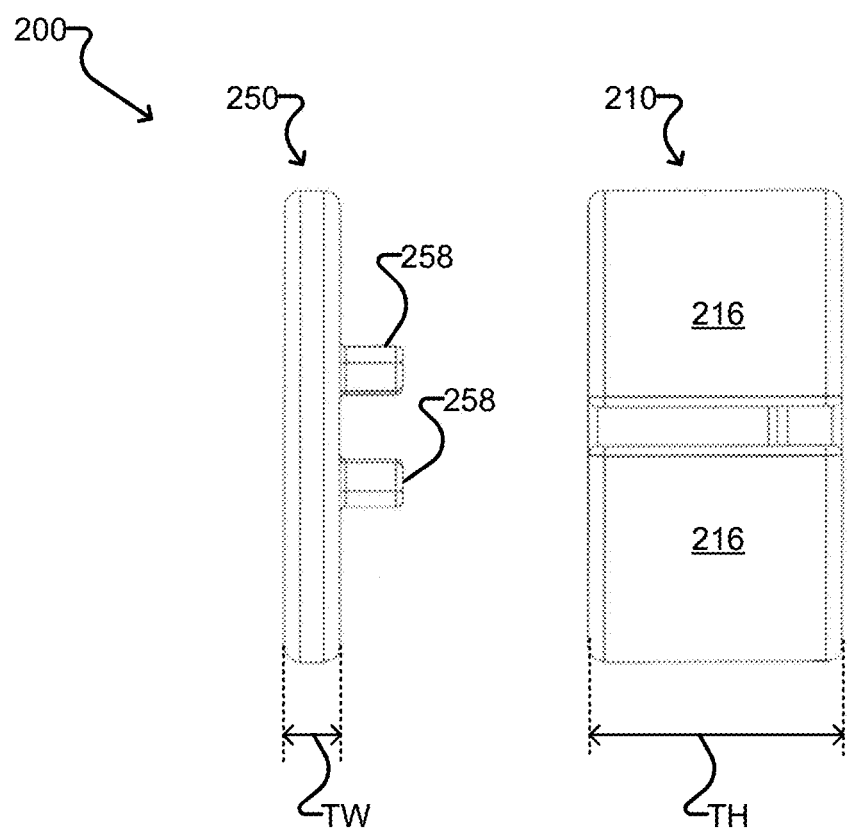
Figure 9:
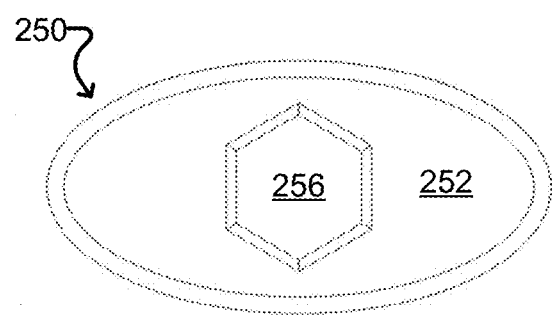
Figure 10A:
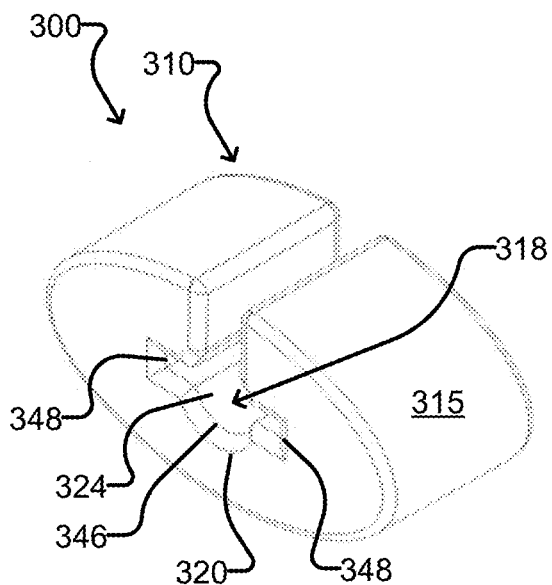
FIG. 10A is a front perspective view of a holder according to an embodiment of the invention.
Figure 10B:
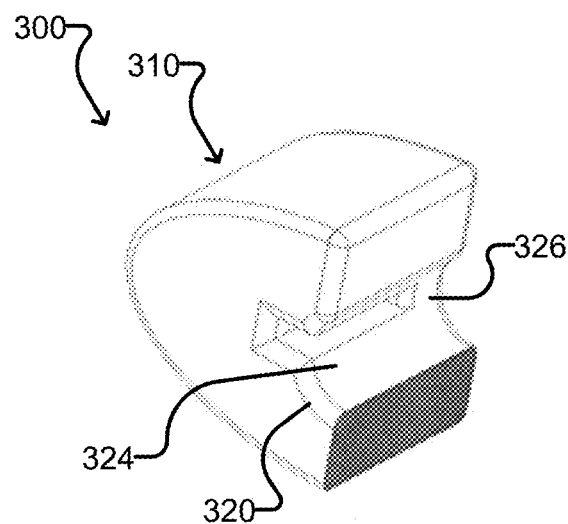
FIG. 10B is a sectional front perspective view of a holder according to the embodiment shown in FIG. 10A.
Figure 10C:
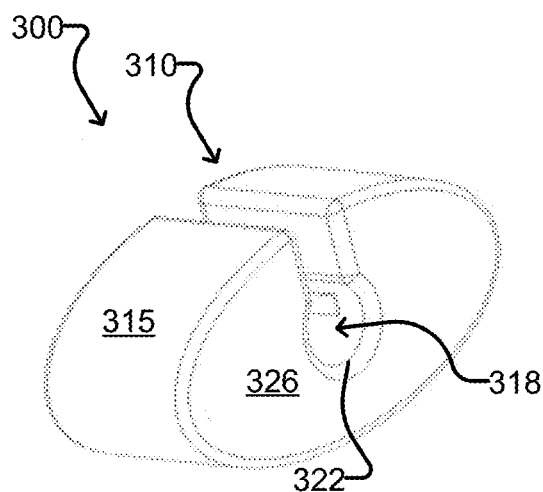
FIG. 10C is a rear perspective view of a holder according to the embodiment shown in FIG. 10A.
Figure 10D:
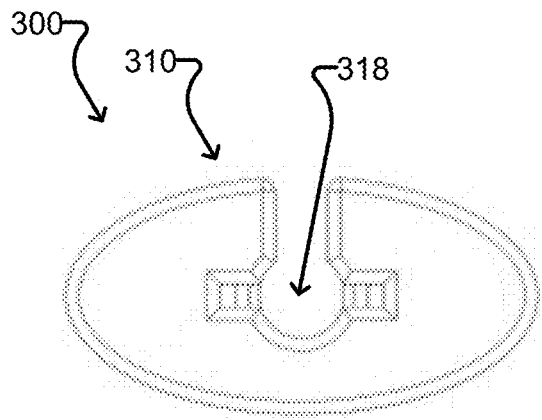
FIG. 10D is a front view of a holder according to the embodiment shown in FIG. 10A.

FIGS. 1A to 10 show typical catheter assemblies at their proximal ends. FIG. 1A shows a catheter assembly C1 with a catheter line L1, valve V1 and a needleless connector N1 threadably connected to valve V1. Valve V1 has a body B1 and a tail T1. Body B1 is a flattened ovoid shape, and tail T1 is cylindrical. FIG. 1B shows a catheter assembly C2 with a catheter line L2, and a valve V2 without a needleless connector connected. Valve V2 has a body B2 and a tail T2. Body B2 is cylindrical with a pair of wings, and tail T2 is cylindrical. FIG. 10 shows a catheter assembly C3 with a catheter line L3, a clamp C3, and a valveless hub H3 without a needleless connector connected. Valveless hub H3 has a body B3. Body B3 is cylindrical with a pair of wings.

Aspects of the present invention are directed to a holder to secure a catheter port during removal of a needleless connector from the catheter port. The holder has a cavity for receiving and accommodating the catheter port, the cavity dimensioned as described herein to prevent the catheter port from rotating and from sliding off in the distal direction. Rotationally locking the catheter port allows a wrench to be used to unthread the needleless connector from the catheter port. The mechanical advantage of the wrench and the holder allows a user to generate sufficient torque to easily disconnect the needleless connector from the catheter port. In some aspects, the holder may be used with any suitable wrench. In other aspects, the holder and the wrench may be provided together as a two-piece tool, and may be detachably coupled to each other when not in use.

FIGS. 2 to 5 show a tool 100 according to an embodiment of the invention. Tool 100 is a holder 110 having a front surface 112, a rear surface 114, and a side surface 115 which includes a top surface 116. A cavity 118 extends through holder 110 from a front opening 120 on the front surface 112 to a rear opening 122 on rear surface 114.

Front opening 120 opens into front section 124 of cavity 118. Front opening 120 is large enough to easily receive a catheter port. Rear opening 122 opens into rear section 126 of cavity 118. Front section 124 and rear section 126 are continuous with each other and are joined at a rear inner wall 128. Rear inner wall 128 is in a plane parallel to front surface 112 and rear surface 114. In some embodiments the rear inner wall may taper from the front section to the rear section.

Front section 124 is dimensioned for clearance fit of a catheter port, for example a body. Here, clearance fit means that there is sufficient clearance between the outer surface of the body and front section 124 to permit reception and accommodation of the body in front section 124 and to also prevent any significant rotation of the body within front section 124. Here, significant rotation means rotation greater than 2 degrees, 5 degrees, or 10 degrees.

In some embodiments front section 124 occupies at least 75% of the length of cavity 118. The cross-sectional dimension of front section 124 is constant along the length of front section 124. The cross-sectional dimension of front section 124 has an aspect ratio (i.e., width to height ratio) of greater than 1, in order to rotationally lock a body received in front section 124. See for example FIG. 3 where width WC of the cross-sectional dimension of front section 124 is greater than height HC of the cross-sectional dimension of front section 124. Rotational locking is possible for catheter ports also having a cross-sectional dimension with an aspect ratio of greater than 1. In some embodiments the aspect ratio of the cross-sectional dimension of front section 124 is at least 4:3. The cross-sectional dimension of front section 124 may be a rectangle, square, polygon, oval, or any of these shapes with wing portions as described below. When the front section includes wing portions, the width dimension of the aspect ratio of the front section includes the width of the wing portions (see for example FIG. 12, where width WC is greater than height HC).

Rear section 126 is dimensioned for clearance fit of a valve tail. Here, clearance fit means that there is sufficient clearance between the outer diameter of the valve tail or the catheter line to permit reception and accommodation of these components in rear section 126 but to restrict movement of the valve tail such that the entire catheter port remains aligned in cavity 118. In some embodiments rear section 126 occupies less than 25% of the length of cavity 118. The cross sectional dimension of rear section 126 is constant along the length of rear section 126. Front section 124 and rear section 126 are co-axial to ensure the catheter port is aligned in cavity 118.

Holder 110 includes a slot 130 adjoining cavity 118. Slot 130 may be centrally aligned above cavity 118. Like cavity 118, slot 130 extends from front surface 112 to rear surface 114 of holder 110. Slot 130 has width WS that is constant along the from front surface 112 to rear surface 114 of holder 110. Width WS may be less than half the width WC of the cross-sectional dimension of front section 124.

In some embodiments, holder 110 has a cross-sectional profile with an aspect ratio (width to height ratio) of at least 3:2, or at least 2:1. For example, holder 110 may have a oval cross-sectional profile or a rectangular cross-sectional profile with such aspect ratios. Such aspect ratios of holder 110 facilitate the application of greater torque by a user when loosening and removing the needleless connector.

In some embodiments, corners of front opening 120 may be bevelled or rounded to facilitate smooth entry of the catheter port into cavity 118. Corners 136 of slot 130 may be bevelled or rounded to facilitate smooth entry of the catheter line into cavity 118.

Inner edges 132 of front section 124, corners 138 of rear inner wall 128 and corners 140 of rear opening 122 may be bevelled or rounded to protect the catheter line as holder 110 is being positioned, to protect the body and valve tail once they are inside cavity 118, as well as to enhance structural integrity of holder 110. Corners 142 of front surface 112 and corners 144 of rear surface 114 may be bevelled or rounded to provide a comfortable grip for users.

FIGS. 6 to 9 show a tool 200 according to an embodiment of the invention. Tool 200 includes a holder 210 and a wrench 250. Holder 210 is similar to holder 110 as described herein. Wrench 250 has a front surface 252, rear surface 254, side surface 255, and a through hole 256. Through hole 256 is hexagonal to lockingly engage needleless connectors with hexagonal profiles. Through hole 256 may be other polygonal or multi-point shapes to provide sufficient contact points with the outer surface of the needleless connector to lockingly or frictionally engage them in a manner that facilitates the application of sufficient torque to loosen and remove the needleless connector.

Through hole 256 may be centrally disposed in wrench 250. The cross-sectional area of through hole 256 may be at least 30% of an area of front surface 252 or rear surface 254 of wrench 250.

Holder 210 and wrench 250 may share a common oval cross-sectional profile. In other embodiments the common cross-sectional profile may be rectangular. Thickness TW of wrench 250 is less than thickness TH of holder 210. In some embodiments, thickness TW of wrench 250 is no greater than 25%, or no greater than 50%, of thickness TH of holder 210.

A pair of opposing C-shaped projections 258 project from rear surface 254 of wrench 250. An inner surface 260 of projections 258 are partially defined by the hexagonal shape of through hole 256. Outer surfaces 262 of projections 258 frictionally engage front opening 220 of cavity 218 in a press fit to detachably couple wrench 250 to holder 210. In other embodiments, wrench 250 and holder 210 may have other arrangements of suitable male/female connectors for frictional engagement, or other suitable engagement, for detachably coupling wrench 250 and holder 210.

In some embodiments, corners 264 of through hole 256, and corners 270 of inner distal end of C-shaped projections 258, may be bevelled or rounded to facilitate smooth engagement between wrench 250 and the needleless connector. Corners 264 of front surface 252, corners 268 of rear surface 254, and corners 272 of outer distal end of C-shaped projections 258, may be bevelled or rounded to provide a comfortable grip and handling for the user. Corners 274 of outer proximal end of C-shaped projections 258 may be bevelled or rounded to enhance structural integrity of C-shaped projections 258.

FIGS. 10A to 10D show a tool 300 according to an embodiment of the invention. Tool 300 is similar to tool 100 as described herein. However, holder 310 has a front opening 320 and front section 324 of cavity 318 different from holder 110's front opening 120 and front section 124 of cavity 118. Front opening 320 and front section 324 have a cross-sectional dimension similar to the cross-sectional dimension of the largest section of a body of a catheter port. In particular, center catheter portion 346 of front section 324 receives and accommodates the center catheter portion of the body, and wing catheter portions 348 receive and accommodate the wings of the body. Front section 324 is dimensioned for clearance fit of a body. Here, clearance fit means that there is sufficient clearance between the outer surface of the body and front section 324 to permit reception and accommodation of the body in front section 324 and to also prevent any significant rotation of the body within front section 324. Here, significant rotation means rotation greater than 2 degrees, 5 degrees, or 10 degrees. Wing catheter portions 348 of front section 324 in particular constrain rotation of the body.

Figure 11:
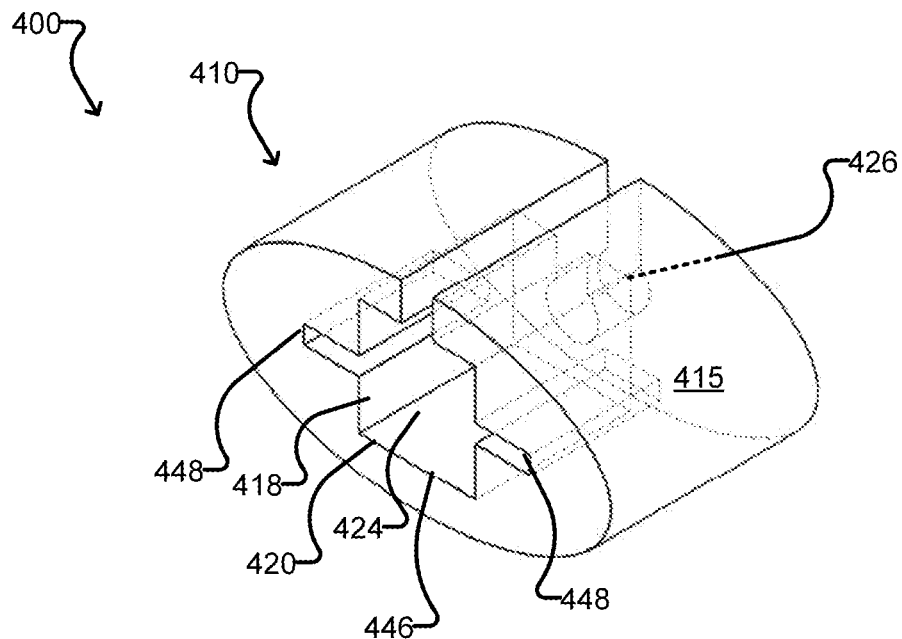
FIG. 11 is a front perspective view of a holder according to an embodiment of the invention.

FIG. 11 shows a tool 400 according to an embodiment of the invention. Tool 400 is similar to tool 300 as described herein. Holder 410 has a front opening 420 and a cavity 418 and a slot with a front section 424 and rear section 426. Front section 424 has a center portion 446 with wing portions 448. Holder 410 differs from holder 310 in that center portion 446 is square instead of circular.

Figure 12:
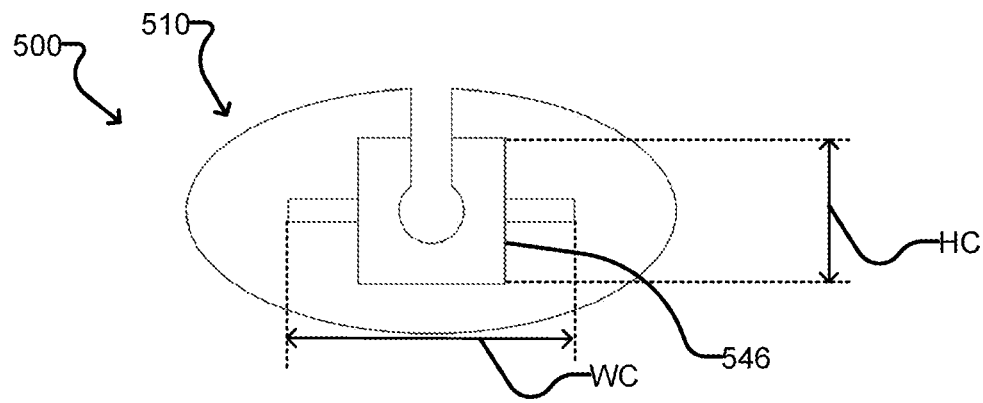
FIG. 12 is a front view of a holder according an embodiment of the invention.

FIG. 12 shows a tool 500 according to an embodiment of the invention. Tool 500 is similar to tool 400 as described herein. Holder 510 differs from holder 410 in that center portion 546 is rectangular instead of square.

Figure 13:
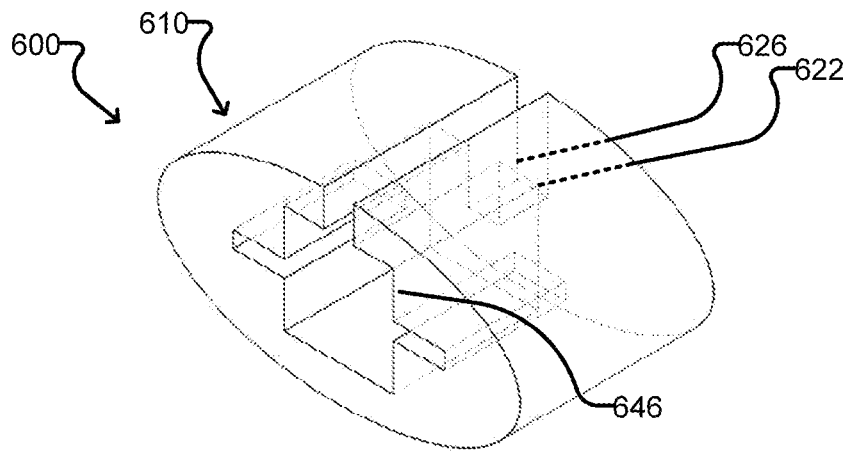
FIG. 13 is a front perspective view of a holder according to an embodiment of the invention.

FIG. 13 shows a tool 600 according to an embodiment of the invention. Tool 600 is similar to tool 400 as described herein. Holder 610 differs from holder 410 in that center portion 646 is rectangular instead of square. Holder 610 also differs from holder 410 in that the cross-section of rear opening 622 and rear section 626 are rectangular instead of circular.

Figure 14:
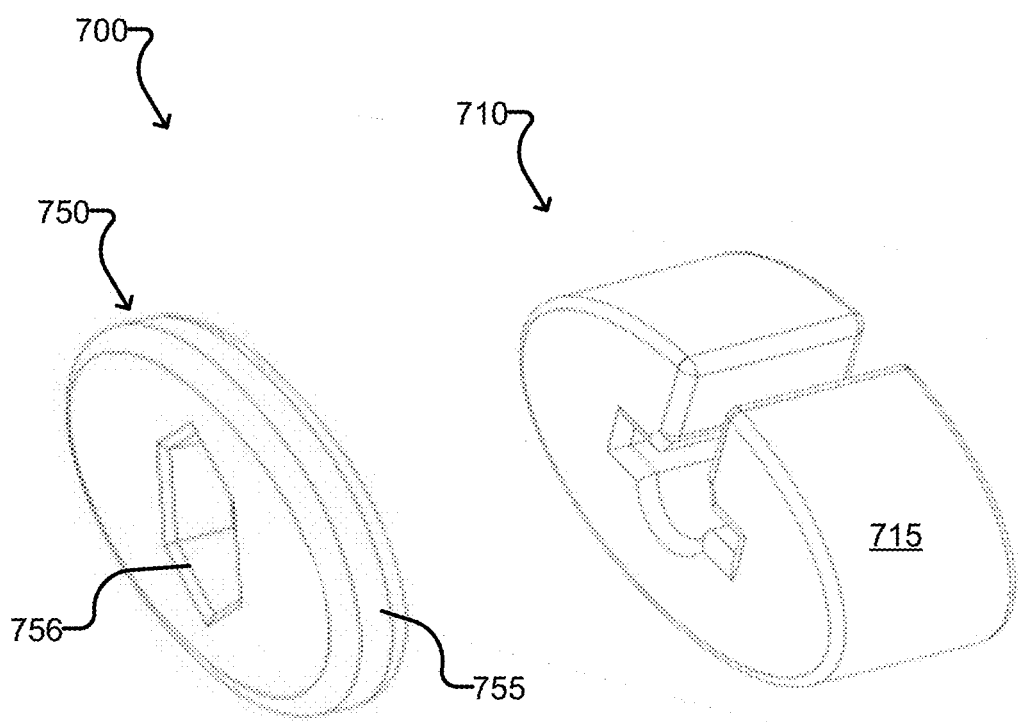
FIG. 14 is a front perspective view of a wrench and holder combination according to an embodiment of the invention.
Figure 15:
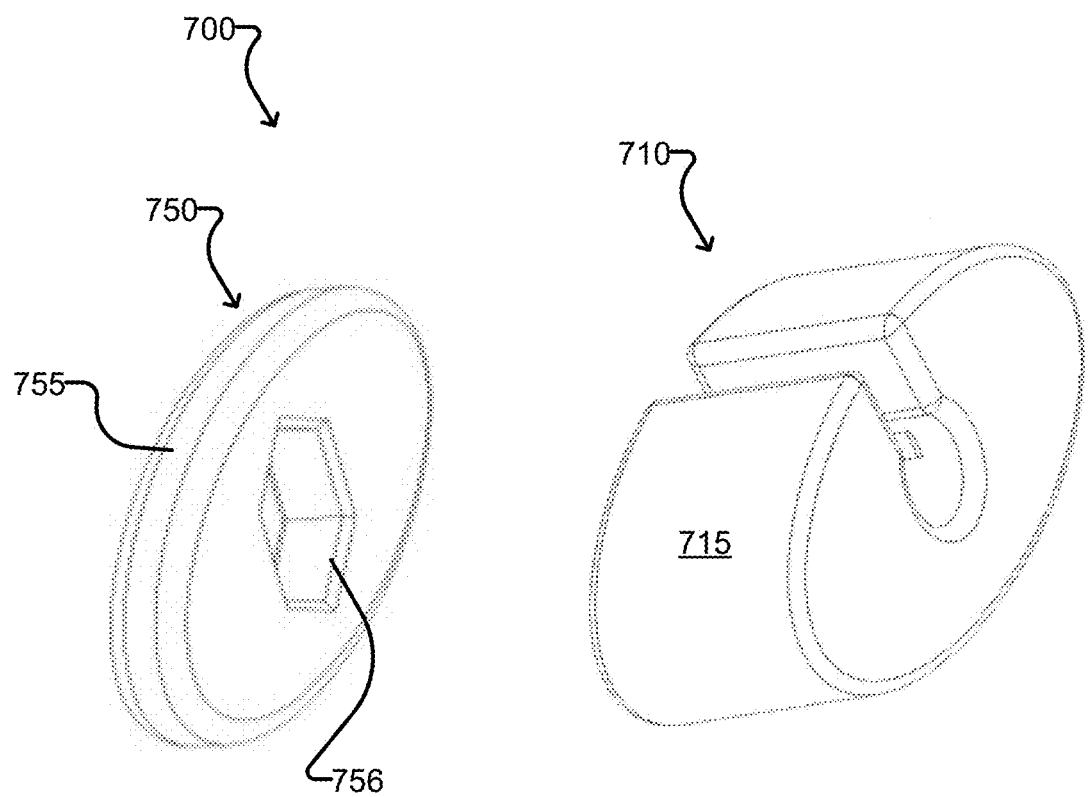
FIG. 15 is a rear perspective view of a wrench and holder combination according to the embodiment shown in FIG. 14.

FIGS. 14 and 15 show a tool 700 according to an embodiment of the invention. Tool 700 includes a holder 710 and a wrench 750. Holder 710 is similar to holder 310, 610, and wrench 750 is similar to wrench 250 as described herein.

As apparent from the illustrations, the aspect ratios of cross-sectional dimension of the front section of the cavity of each of holders 310, 410, 510, 610 and 710 is greater than 1, or at least 4:3, due to the additional width provided by the wing portions.

Figure 16:
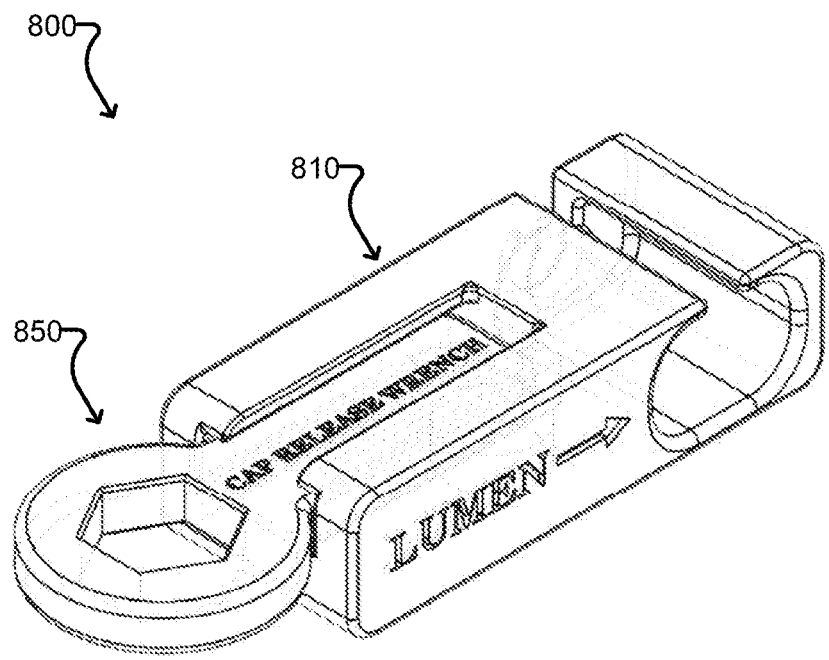
FIG. 16 is a perspective view of a wrench and holder combination in an storage configuration according to an embodiment of the invention.
Figure 17:
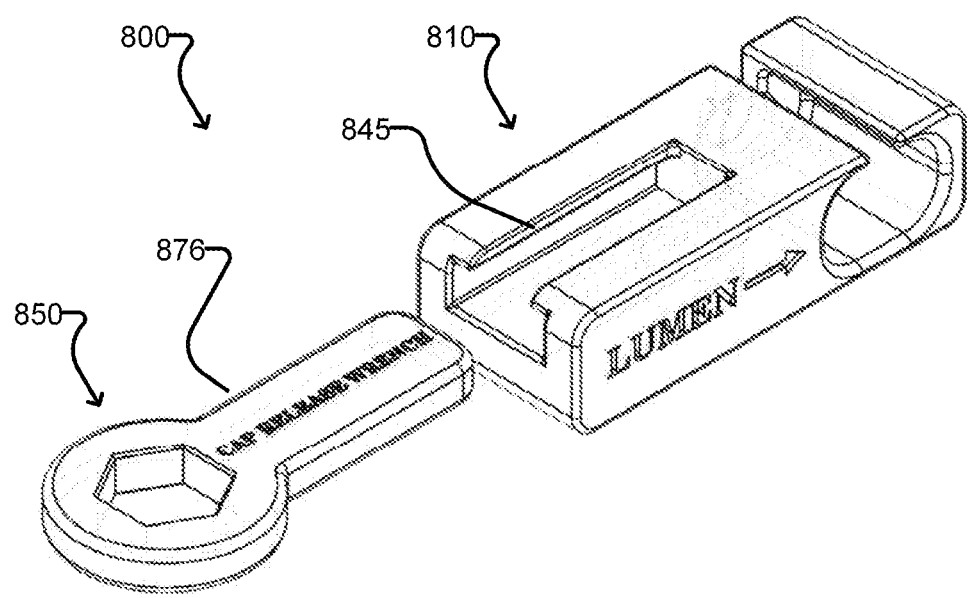
FIG. 17 is a perspective view of a wrench and holder combination in a ready-to-use configuration according to the embodiment shown in FIG. 16.

FIGS. 16 and 17 show a tool 800 according to an embodiment of the invention. Tool 800 includes a holder 810 and a wrench 850. Holder 810 functions similarly to holder 110. Wrench 850 is similar to wrench 250, 750 but has a handle 876. Holder 810 has a slot 845 which receives handle 876 of wrench 850 when not in use.

The material used for tools 100, 200, 300, 400, 500, 600, 700 and 800 may be one or more of biocompatible, medical grade and food safe. The material may be a plastic material. The material may not be harder than the material of the needleless connector and the catheter port. In some embodiments tools 100, 200, 300, 400, 500, 600, 700 and 800 may be 3D printed using a resin-based engineering plastic material softer than the catheter line to prevent marking up or otherwise damaging the catheter line. In some embodiments tools 100, 200, 300, 400, 500, 600, 700 and 800 may be reusable, and in other embodiments disposable after a single use.

Catheter portions, or the entirety, of surfaces of tools 100, 200, 300, 400, 500, 600, 700 and 800 which are gripped by a user (e.g. side surfaces 115, 215, 315 and 415, and side surfaces 255 and 755) may be provided with grip-enhancing surface features such as ridges, nubs and the like. Such features can provide better grip (and less slippage), as well as increase torque that can be applied by the user. In the illustrated embodiments these surfaces are smooth.

Figure 18:
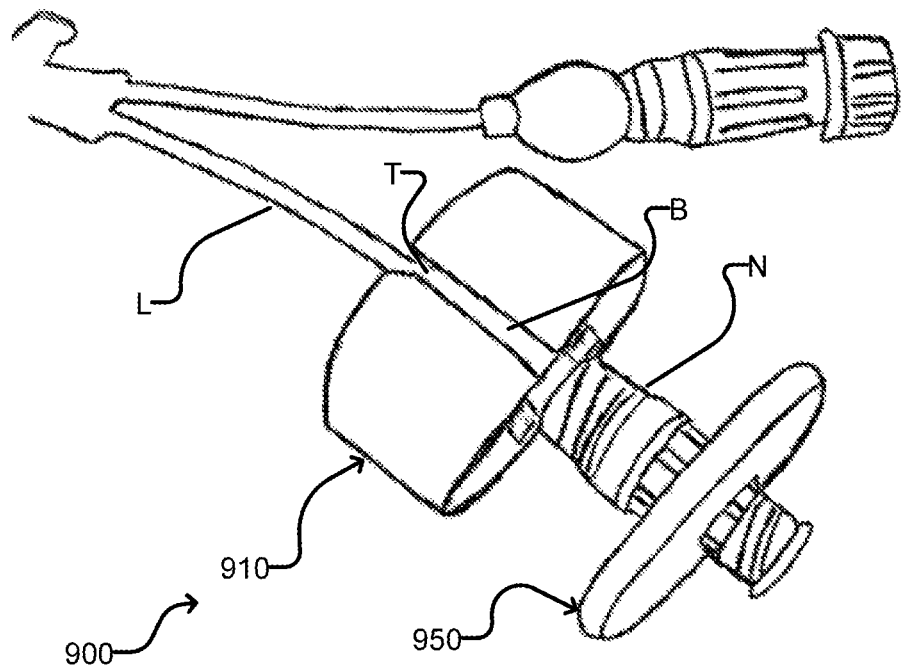
FIG. 18 is an image of a catheter assembly engaged by a wrench and holder combination according to an embodiment of the invention.

FIG. 18 shows a tool 900 in operation. Holder 910 is similar to holder 110. Wrench 950 is similar to wrench 750. To remove needleless connector N from the catheter port (here, a valve with body B and tail T), first holder 910 is placed adjacent to catheter line L distal to the valve such that catheter line L can slip into the slot of holder 910. Next, holder 910 is slid proximally toward the valve. The front opening of holder 910 is oriented to receive the valve into the cavity of holder 910. Holder 910 is slid proximally until the inner rear wall of holder 910 abuts the proximal end of body B of the valve. Thus tail T is received in the rear section, and body B is received in the front section, of the cavity of holder 910, and due to the respective dimensions of body B and the front section, the valve is "locked in", and prevented from any significant rotation within the cavity. The valve is also "locked in" in since it cannot move in the proximal direction since it is abutting the rear inner wall of the cavity. At this point a suitable means can be used to grasp the needleless connector N and twist it off the valve. For example, a wrench such as wrench 950 may be used. In other embodiments, any suitable wrench that may be used. In other embodiments, any tool that can grasp the needleless connector may be used. In other embodiments, a user may use their available hand (the other hand holding the holder) to grasp and twist off the needleless connector.

Figure 19:
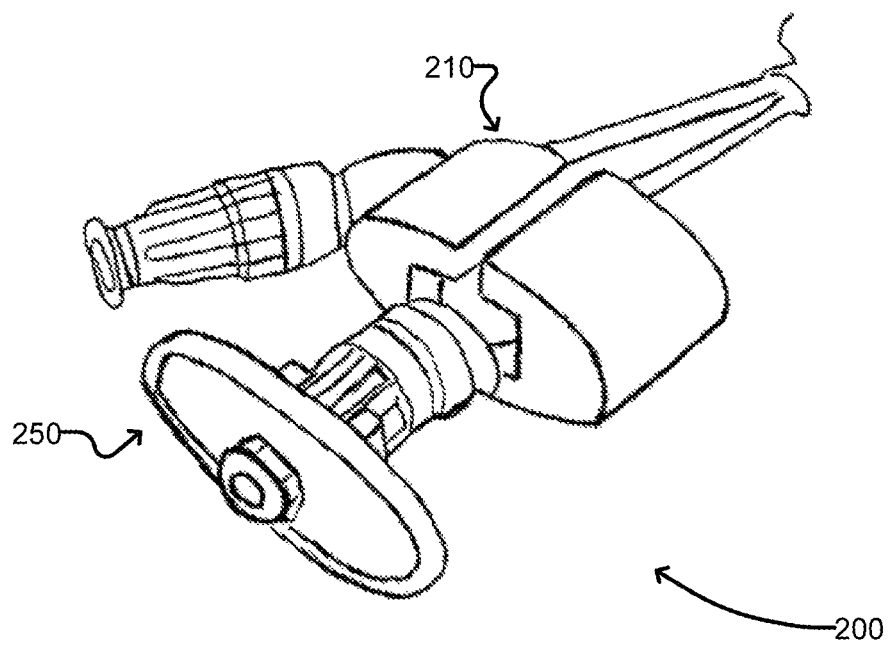
FIG. 19 is an image of a catheter assembly engaged by a wrench and holder combination according to an embodiment shown in FIG. 6.

FIG. 19 shows tool 200 in operation. Holder 210 operates in a similar manner to holder 910, and wrench 250 operates in a similar manner to wrench 950.

FIGS. 18 and 19 show the use of the holder of the invention with bulb valves as catheter ports. Other embodiments of the holder may be used with catheter ports of other types of shapes in a similar manner. For example, catheter ports with wings (such as with catheter assemblies C2 and C3 in FIG. 1), holders such as holder 310, 410, 510, 610 and 710 may be used, with or without a wrench such as wrench 250, 450, 950. The center catheter portions of the front section receive the tubular section of the catheter ports, while the wing catheter portions of the front section receive the wing sections of the catheter ports. The catheter ports are rotationally locked within the front section of the cavity due to the wing sections of the catheter ports being constrained within the wing catheter portions of the cavity. The catheter ports are also "locked in" in since they cannot move in the proximal direction since they would be abutting the rear inner wall of the cavity.

Figure 20:
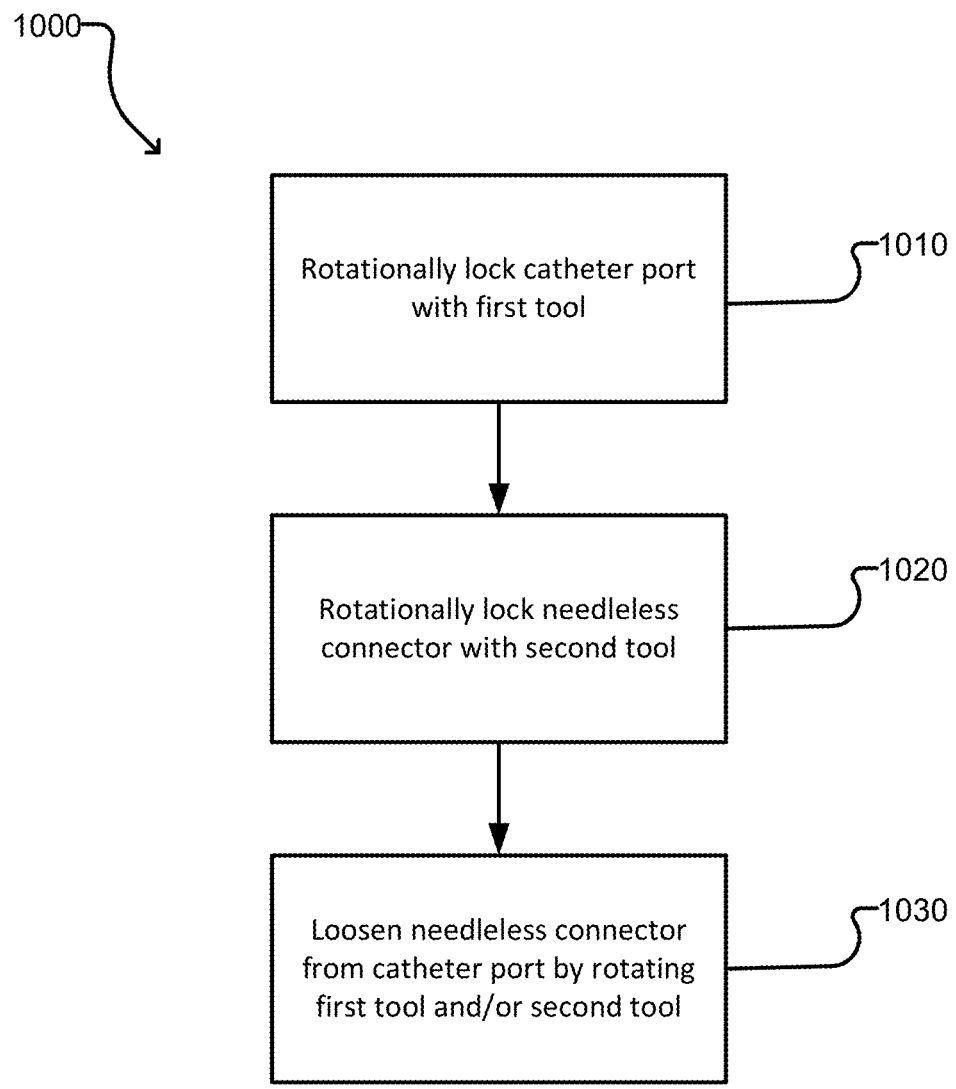
FIG. 20 is a flow diagram of a method for loosening a needleless connector according to an embodiment.

FIG. 20 shows a method 1000 for loosening a needleless connector according to an embodiment of the invention. In step 1010, a user guides a first tool onto a catheter port to engage and rotationally lock the catheter port. In step 1020, the user positions a second tool to engage and rotationally lock the needleless connector. In step 1030, the user rotates the first tool and/or the second tool to loosen the needleless connector from the catheter port.

In some embodiments, step 1010 may include at least partially accommodating the catheter port in an opening of the first tool, wherein the opening is dimensioned to lockingly engage the catheter port. In some embodiments, a cross-sectional dimension of the opening may have an aspect ratio of at least 1 to lockingly engage a catheter port having a cross-sectional dimension of at least 1. In some embodiments, step 1010 may include securing the first tool from sliding away from the catheter port in the proximal direction, wherein the opening comprises a rear inner wall against which the distal end of the catheter port abuts when the catheter port is at least partially accommodated within the cavity. In some embodiments, step 1030 may involve the user holding the first tool still and rotating the second tool, or holding the second tool still and rotating the first tool, or rotating the first tool and the second tool in opposite directions. In some embodiments, method 1000 may be accomplished using any one of tools 100, 200, 300, 400, 500, 600, 700, 800 and 900. In other embodiments, method 1000 may be accomplished using other suitable tools.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are consistent with the broadest interpretation of the specification as a whole.

The invention claimed is:

1. A tool for loosening a needleless connector, the tool comprising:
   a holder for holding a catheter port, the holder comprising:
      a front surface,
      a rear surface,
      a top surface,
      a cavity for accommodating the catheter port, the cavity extending through the holder and comprising a front opening in the front surface, a rear opening in the rear surface, and a rear inner wall,
      wherein the cavity is defined by at least a first cross-sectional dimension and a second cross-sectional dimension, the first cross-sectional dimension at least partially defining a front section opening to the front opening, the second cross-sectional dimension at least partially defining a rear section opening to the rear opening, wherein the first cross-sectional dimension is greater in area than the second cross-sectional dimension, the rear inner wall defining the narrowing of the front section to the rear section, the rear inner wall normal to a longitudinal axis of the cavity, wherein the first cross-sectional dimension has an aspect ratio of greater than 1, whereby the front section frictionally or lockingly engages the catheter port, and a slot in the top surface extending from the front surface to the rear surface, the slot adjoining the cavity.

2. The tool according to claim 1, wherein the first cross-sectional dimension is constant along the front section, the second cross-sectional dimension is constant along the rear section.

3. The tool according to claim 2, wherein the rear inner wall is parallel to the front surface and the rear surface.

4. The tool according to claim 3, wherein the first cross-sectional dimension has an aspect ratio of at least 4:3.

5. The tool according to claim 4, wherein the first cross-sectional dimension has a central portion with opposing wing portions.

6. The tool according to claim 5, wherein the cross-sectional profile of the holder is an oval or a rectangle having an aspect ratio of at least 3:2.

7. The tool according to claim 6, wherein the front section and the rear section of the cavity are co-axial.

8. The tool according to claim 7, wherein the slot is centrally aligned above the cavity.

9. The tool according to claim 8 wherein a width of the slot is constant from the front surface to the rear surface of the holder.

10. The tool according to claim 9, wherein a width of the slot is less than a half of a width of the first cross-sectional dimension.

11. The tool according to claim 10, wherein corners between the front opening and the cavity, between the rear opening and the cavity, between the slot and the top surface, and between the slot and the cavity, are bevelled or rounded.

12. A tool for loosening a needleless connector, the tool comprising;

a holder for holding a catheter port, the holder comprising:

a front surface, a rear surface, a top surface, a cavity for accommodating the catheter port, the cavity extending through the holder and comprising a front opening in the front surface, a rear opening in the rear surface, and a rear inner wall, wherein the cavity is defined by at least a first cross-sectional dimension and a second cross-sectional dimension, the first cross-sectional dimension at least partially defining a front section opening to the front opening, the second cross-sectional dimension at least partially defining a rear section opening to the rear opening, wherein the first cross-sectional dimension is greater in area than the second cross-sectional dimension, the rear inner wall defining the narrowing of the front section to the rear section, wherein the first cross-sectional dimension has an aspect ratio of greater than 1, whereby the front section frictionally or lockingly engages the catheter port, and a slot in the top surface extending from the front surface to the rear surface, the slot adjoining the cavity, a wrench for gripping the needleless connector, the wrench comprising a front surface, a rear surface, and a through hole, wherein the holder and the wrench are separate components capable of independently manipulation.

13. The tool of claim 12, wherein the through hole is configured to frictionally or lockingly engage the needleless connector.

* * * * *